(12) United States Patent
Shellenberger et al.

(10) Patent No.: US 10,925,616 B2
(45) Date of Patent: Feb. 23, 2021

(54) CLIP APPLIER WITH REPLACEABLE TIPS

(71) Applicant: TELEFLEX MEDICAL INCORPORATED, Morrisville, NC (US)

(72) Inventors: Carson J. Shellenberger, Cary, NC (US); Warren Taylor, Cary, NC (US); David Lee Foshee, Apex, NC (US)

(73) Assignee: Teleflex Medical Incorporated, Morrisville, NC (US)

( * ) Notice: Subject to any disclaimer, the term of this patent is extended or adjusted under 35 U.S.C. 154(b) by 12 days.

(21) Appl. No.: 15/927,660

(22) Filed: Mar. 21, 2018

(65) Prior Publication Data
US 2018/0271535 A1    Sep. 27, 2018

Related U.S. Application Data

(60) Provisional application No. 62/474,505, filed on Mar. 21, 2017.

(51) Int. Cl.
*A61B 17/128* (2006.01)
*A61B 17/122* (2006.01)
(Continued)

(52) U.S. Cl.
CPC ........ *A61B 17/1285* (2013.01); *A61B 17/122* (2013.01); *A61B 17/1222* (2013.01);
(Continued)

(58) Field of Classification Search
CPC .............. A61B 17/122; A61B 17/1222; A61B 17/1227; A61B 17/1285;
(Continued)

(56) References Cited

U.S. PATENT DOCUMENTS

| 929,868 A | 8/1909 | Mueller |
|---|---|---|
| 1,482,290 A | 1/1924 | Elzi |

(Continued)

FOREIGN PATENT DOCUMENTS

| CN | 101543418 A | 9/2009 |
|---|---|---|
| CN | 106037947 A | 10/2016 |

(Continued)

OTHER PUBLICATIONS

International Search Report (ISR) (PCT Form PCT/ISA/210) dated May 31, 2018, in PCTUS2018/023593.

(Continued)

*Primary Examiner* — George J Ulsh
(74) *Attorney, Agent, or Firm* — BakerHostetler (57) ABSTRACT

A method of securing a surgical clip to a clip applier may include engaging a first applier tip with a first jaw member, and engaging a second applier tip with a second jaw member. The jaw members may be secured within sleeve portions of the applier tips. The surgical clip may then be received between the first and second jaw members and secured with the first and second applier tips. The surgical clip may be secured to the clip applier by receiving a proximal portion of the surgical clip between a first protrusion of the first applier tip and a second protrusion of the second applier tip, receiving a first boss member on a first leg member of the surgical clip in a recess of the first applier tip, and receiving a second boss member on a second leg member of the surgical clip in a recess of the second applier tip.

20 Claims, 5 Drawing Sheets (51) Int. Cl.
*A61B 17/00* (2006.01)
*A61B 17/28* (2006.01)
*A61B 17/29* (2006.01)
*A61B 50/36* (2016.01)

(52) U.S. Cl.
CPC .......... *A61B 17/1227* (2013.01); *A61B 17/28* (2013.01); *A61B 17/282* (2013.01); *A61B 50/36* (2016.02); *A61B 2017/00296* (2013.01); *A61B 2017/00473* (2013.01); *A61B 2017/2825* (2013.01); *A61B 2017/2926* (2013.01)

(58) Field of Classification Search
CPC .......... A61B 2017/00296; A61B 2017/00473; A61B 17/28; A61B 17/282; A61B 2017/2825; A61B 2017/2926; A61B 50/36; A61B 17/128
See application file for complete search history.

(56) References Cited

U.S. PATENT DOCUMENTS

| | | |
|---|---|---|
| 2,384,697 A | 9/1945 | Riccardi |
| 2,594,102 A | 4/1952 | Vollmer |
| 2,598,901 A | 6/1952 | Garland |
| 2,626,608 A | 1/1953 | Garland |
| 2,635,238 A | 4/1953 | Garland |
| 2,744,251 A | 5/1956 | Vollmer |
| 2,814,222 A | 11/1957 | Sanders |
| 2,881,762 A | 4/1959 | Lowrie |
| 2,890,519 A | 6/1959 | Storz |
| 3,032,039 A | 5/1962 | Beaty |
| 3,150,379 A | 9/1964 | Brown |
| 3,172,133 A | 3/1965 | Rizzo |
| 3,446,212 A | 5/1969 | Pierre |
| 3,463,156 A | 8/1969 | Mcdermott |
| 3,503,396 A | 3/1970 | Pierie |
| 3,503,397 A | 3/1970 | Fogarty et al. |
| 3,503,398 A | 3/1970 | Fogarty |
| 3,827,438 A | 8/1974 | Kees, Jr. |
| 3,867,944 A | 2/1975 | Samuels |
| 3,954,108 A | 5/1976 | Davis |
| 4,120,302 A | 10/1978 | Ziegler |
| 4,274,415 A | 6/1981 | Kanamoto |
| 4,316,468 A | 2/1982 | Klieman et al. |
| 4,325,376 A | 4/1982 | Klieman et al. |
| 4,337,774 A | 7/1982 | Perlin |
| 4,414,721 A | 11/1983 | Hufnagel |
| 4,428,374 A | 1/1984 | Auburn |
| 4,444,187 A | 4/1984 | Perlin |
| 4,471,780 A | 9/1984 | Menges et al. |
| 4,487,204 A | 12/1984 | Hrouda |
| 4,534,351 A | 8/1985 | Rothfuss et al. |
| 4,570,633 A | 2/1986 | Golden |
| 4,616,651 A | 10/1986 | Golden |
| 4,671,281 A | 6/1987 | Beroff et al. |
| 4,686,983 A | 8/1987 | Leisman et al. |
| 4,834,090 A | 5/1989 | Moore |
| 4,834,096 A | 5/1989 | Oh et al. |
| 4,854,317 A | 8/1989 | Braun |
| 4,870,965 A | 10/1989 | Jahanger |
| 4,919,152 A | 4/1990 | Ger |
| 4,924,864 A | 5/1990 | Danzig |
| 4,934,364 A | 6/1990 | Green |
| 4,976,722 A | 12/1990 | Failla |
| 5,009,657 A | 4/1991 | Cotey et al. |
| 5,062,846 A | 11/1991 | Oh et al. |
| 5,100,416 A | 3/1992 | Oh et al. |
| 5,141,514 A | 8/1992 | van Amelsfort |
| 5,207,692 A | 5/1993 | Kraus et al. |
| 5,246,450 A | 9/1993 | Thornton et al. |
| 5,431,668 A | 7/1995 | Burbank, III et al. |
| 5,462,555 A | 10/1995 | Bolanos et al. |
| 5,464,416 A | 11/1995 | Steckel |
| 5,569,274 A | 10/1996 | Rapacki et al. |
| 5,575,796 A | 11/1996 | King et al. |
| 5,591,178 A | 1/1997 | Green et al. |
| 5,607,436 A | 3/1997 | Pratt et al. |
| 5,626,585 A | 5/1997 | Mittelstadt et al. |
| 5,797,922 A | 8/1998 | Hessel et al. |
| 5,843,097 A | 12/1998 | Mayenberger et al. |
| 5,925,052 A | 7/1999 | Simmons |
| 5,972,003 A | 10/1999 | Rousseau et al. |
| 6,010,516 A | 1/2000 | Hulka |
| 6,013,088 A | 1/2000 | Karavidas |
| 6,050,996 A | 4/2000 | Schmaltz et al. |
| 6,217,590 B1 | 4/2001 | Levinson |
| 6,228,104 B1 | 5/2001 | Fogarty et al. |
| 6,258,105 B1 | 7/2001 | Hart et al. |
| 6,273,887 B1 | 8/2001 | Yamauchi et al. |
| 6,273,902 B1 | 8/2001 | Fogarty et al. |
| 6,277,117 B1 | 8/2001 | Tetzlaff et al. |
| 6,352,541 B1 | 3/2002 | Kienzle et al. |
| 6,387,112 B1 | 5/2002 | Fogarty et al. |
| 6,391,035 B1 | 5/2002 | Appleby |
| 6,558,408 B1 | 5/2003 | Fogarty et al. |
| 6,814,742 B2 | 11/2004 | Kimura et al. |
| 6,824,547 B2 | 11/2004 | Wilson, Jr. et al. |
| 6,837,895 B2 | 1/2005 | Mayenberger |
| 6,880,699 B2 | 4/2005 | Gallagher |
| 6,926,712 B2 | 8/2005 | Phan |
| 6,932,816 B2 | 8/2005 | Phan |
| 7,001,412 B2 | 2/2006 | Gallagher et al. |
| 7,052,504 B2 | 5/2006 | Hughett |
| 7,094,245 B2 | 8/2006 | Adams et al. |
| 7,108,699 B2 | 9/2006 | Kobayashi |
| 7,179,265 B2 | 2/2007 | Manetakis et al. |
| 7,211,092 B2 | 5/2007 | Hughett |
| 7,316,696 B2 | 1/2008 | Wilson, Jr. et al. |
| 7,326,223 B2 | 2/2008 | Wilson, Jr. |
| 7,357,805 B2 | 4/2008 | Masuda et al. |
| 7,572,266 B2 | 8/2009 | Young et al. |
| 7,585,304 B2 | 9/2009 | Hughett |
| 7,645,285 B2 | 1/2010 | Cosgrove et al. |
| 7,648,514 B1 | 1/2010 | Nakao |
| 7,727,231 B2 | 6/2010 | Swanson |
| 7,753,908 B2 | 7/2010 | Swanson |
| 7,785,324 B2 | 8/2010 | Eberl |
| 8,425,412 B2 | 4/2013 | Rucker |
| 8,512,357 B2 | 8/2013 | Viola |
| 8,585,718 B2 | 11/2013 | Disch et al. |
| 8,764,774 B2 | 7/2014 | Sigmon, Jr. |
| 8,852,216 B2 | 10/2014 | Cropper et al. |
| 8,894,666 B2 | 11/2014 | Schulz et al. |
| 8,900,253 B2 | 12/2014 | Aranyi et al. |
| 8,945,151 B2 | 2/2015 | Salas |
| 8,992,566 B2 | 3/2015 | Baldwin |
| 9,271,737 B2 | 3/2016 | Castro et al. |
| 9,445,820 B2 | 9/2016 | Whiting |
| 9,456,824 B2 | 10/2016 | Willett et al. |
| 9,737,309 B1 | 8/2017 | Ad |
| 9,855,053 B2 | 1/2018 | Bagaoisan et al. |
| 9,955,977 B2 | 5/2018 | Martinez et al. |
| 10,136,898 B2 | 11/2018 | Schmidt et al. |
| 10,292,712 B2 | 5/2019 | Shankarsetty |
| 10,383,637 B2 | 8/2019 | Castro |
| 10,758,243 B2 | 9/2020 | Salas |
| 2002/0169459 A1 | 11/2002 | Porat |
| 2003/0158548 A1 | 8/2003 | Phan et al. |
| 2004/0097970 A1 | 5/2004 | Hughett |
| 2005/0090838 A1 | 4/2005 | Sixto, Jr. et al. |
| 2005/0149068 A1 | 7/2005 | Williams et al. |
| 2005/0165421 A1 | 7/2005 | Wilson, Jr. et al. |
| 2005/0165423 A1 | 7/2005 | Gallagher et al. |
| 2005/0171560 A1 | 8/2005 | Hughett |
| 2005/0234478 A1 | 10/2005 | Wixey et al. |
| 2006/0217749 A1 | 9/2006 | Wilson et al. |
| 2007/0282355 A1 | 12/2007 | Brown et al. |
| 2009/0112233 A1 | 4/2009 | Xiao |
| 2010/0057107 A1 | 3/2010 | Sorrentino |
| 2010/0274262 A1 | 10/2010 | Schulz et al. |
| 2010/0274264 A1 | 10/2010 | Schulz et al. |
| 2011/0087244 A1 | 4/2011 | Weisshaupt et al. |
| 2011/0144665 A1 | 6/2011 | Malkowski |

(56) References Cited

U.S. PATENT DOCUMENTS

| | | |
|---|---|---|
| 2012/0083803 A1 | 4/2012 | Patel et al. |
| 2012/0226291 A1 | 9/2012 | Malizia et al. |
| 2012/0277765 A1 | 11/2012 | Zammataro et al. |
| 2012/0330326 A1 | 12/2012 | Creston et al. |
| 2013/0261642 A1 | 10/2013 | Willett et al. |
| 2014/0058411 A1 | 2/2014 | Soutorine et al. |
| 2014/0207156 A1 | 7/2014 | Malkowski |
| 2014/0309677 A1 | 10/2014 | Baldwin |
| 2015/0066057 A1 | 3/2015 | Rockrohr et al. |
| 2016/0270790 A1 | 9/2016 | Jankowski |
| 2017/0014135 A1 | 1/2017 | Martin et al. |
| 2018/0036008 A1 | 2/2018 | Ramsey et al. |

FOREIGN PATENT DOCUMENTS

| | | |
|---|---|---|
| GB | 2353710 A | 3/2001 |
| WO | 9738634 A1 | 10/1997 |
| WO | 2005107613 A1 | 11/2005 |
| WO | 2013040467 A2 | 3/2013 |

OTHER PUBLICATIONS

Partial Supplementary Search Report issued in European Application No. 18771180.9, dated Dec. 2, 2020.

CLIP APPLIER WITH REPLACEABLE TIPS

PRIORITY

The present non-provisional patent application claims priority to U.S. Provisional Patent Application No. 62/474,505, filed on Mar. 21, 2017 and now expired, entitled "CLIP APPLIER WITH REPLACEABLE TIPS", the entirety of the disclosure of which is incorporated herein.

TECHNICAL FIELD

The present disclosure relates generally to clip applier devices, and more particularly, to clip applier devices having replaceable tips configured to secure surgical clips.

BACKGROUND

Ligation of tissue (e.g., blood vessels, lymph nodes, nerves, fallopian tubes, and cardiac tissue) is a common practice for many surgical procedures. This can be performed by closing the vessel with a surgical clip or by suturing the vessel with the surgical thread. The use of surgical thread requires complex manipulations of a needle and surgical thread to form knots required to secure the vessel. Such complex manipulations are time consuming and difficult to perform, particularly endoscopic surgical procedures characterized by limited space and/or visibility. In contrast, surgical clips are relatively quick and easy to apply. Accordingly, the use of surgical clips in endoscopic and open surgical procedures has grown dramatically.

SUMMARY

The present inventors recognize that there is a need to improve one or more features of the surgical clips, such as stability of the surgical clip in a clip applier. Currently available clip appliers often secure the clip with two points of contact between opposing jaws of the clip applier and leg members of the clip. This engagement is insufficient because the clip can often rotate to become laterally misaligned or even fall out of the clip applier during use. Furthermore, each of the points of contact often relies on a snap or interference fit between a boss member on the clip and a recess on the clip applier. The recess can often loosen after multiple uses, which would even further reduce the stability of the clip. The disclosed methods and devices are directed to mitigating or overcoming one or more of the problems set forth above and/or other problems in the prior art.

A first aspect of the present disclosure is directed to a method of securing a clip to a clip applier having first and second jaw members. The method may include engaging a first applier tip with the first jaw member, and engaging a second applier tip with the second jaw member. The method may further include receiving the clip between the first and second jaw members, and securing the clip with the first and second applier tips to the clip applier.

In some embodiments, the method may further include aligning the surgical clip by receiving a proximal portion of the surgical clip between a first protrusion of the first applier tip and a second protrusion of the second applier tip. In some embodiments, securing the surgical clip with the first applier tip may include receiving a first boss member on a first leg member of the surgical clip in a recess of the first applier tip, and securing the surgical clip with the second applier tip may include receiving a second boss member on a second leg member of the surgical clip in a recess of the second applier tip. In some embodiments, the method may further include inserting the first and second jaw members into at least one first compartment of a cartridge to engage the first applier tip and the second applier tip, and inserting the first and second jaw members into a second compartment of the cartridge to receive the surgical clip between the first and second jaw members. In some embodiments, the method may include inserting the first jaw member into a first sleeve portion of the first applier tip; and inserting the second jaw member into a second sleeve portion of the second applier tip. In some embodiments, engaging the first applier tip may include releasably securing an engaging member on the first applier tip to an engaging member on the first jaw member, and engaging the second applier tip may include releasably securing an engaging member on the second applier tip to an engaging member on the second jaw member. In some embodiments, engaging the first applier tip may include deflecting a first flexible arm of the first applier tip and receiving a projection on the first flexible arm in a recess of the first jaw member, and engaging the second applier tip may include deflecting a second flexible arm of the second applier tip and receiving a projection on the second flexible arm in a recess of the second jaw member. In some embodiments, the method may include approximating the first and second jaw members to compress the surgical clip, removing the first applier tip from the first jaw members, and removing the second applier tip from the second jaw member.

A second aspect of the present disclosure is directed to a clip applier device configured to be loaded with a surgical clip. The clip applier device may include a clip applier having first and second jaw members, a first applier tip releasably secured to the first jaw member, and a second applier tip releasably secured to the second jaw member. The first and second applier tips may be configured to secure the surgical clip between the first and second jaw members.

In some embodiments, the first applier tip may include a first protrusion extending from an inner surface, the second applier tip may include a second protrusion extending from an inner surface, the first and second protrusions may be configured to receive a proximal portion of the surgical clip therebetween to reduce lateral movement of the surgical clip. In some embodiments, the first and second protrusions may extend off-center of a longitudinal axis of the applier tip. In some embodiments, the first applier tip may include a first recess at a distal portion configured to receive a boss member on the first leg member, and the second applier tip may include a second recess at a distal portion configured to receive a boss member on the second leg member. In some embodiments, the first applier tip may include a first sleeve portion receiving the first jaw member, and the second applier tip may include a second sleeve portion receiving the second jaw member. In some embodiments, the first sleeve portion may include an engaging member releasably secured to an engaging member of the first jaw member, and the second sleeve portion may include an engaging member releasably secured to an engaging member of the second jaw member. The engaging member of the first sleeve portion may include a first flexible arm having a first projection, the engaging member of the first jaw member may include a first recess receiving the first projection, the engaging member of the second sleeve portion may include a second flexible arm having a second projection, and the engaging member of the second jaw member may include a second recess receiving the second projection. In some embodiments, the first sleeve portion may be on a proximal portion of the first applier tip and extend less than an entire length of the first applier tip, and the second sleeve portion may be on a proximal portion of the second applier tip and extend less than an entire length of the second applier tip.

A third aspect of the present disclosure is directed to an applier tip that may be secured to a jaw member of a clip applier and secure a surgical clip to the clip applier. The applier tip may include a sleeve portion configured to receive the jaw member of the clip applier. The applier tip may also include a protrusion extending from an inner surface and configured to engage a proximal portion of the clip.

In some embodiments, the protrusion may extend off-center of a longitudinal axis of the applier tip. In some embodiments the applier tip may include a recess at a distal portion configured to receive a boss member on the surgical clip. In some embodiments, the engaging member of the sleeve portion may include a flexible arm having a projection configured to engage a recess on the jaw member of the surgical clip applier.

A fourth aspect of the present disclosure is directed to a cartridge. The cartridge may include at least one tip compartment containing an applier tip and a clip compartment containing a surgical clip.

BRIEF DESCRIPTION OF THE DRAWINGS

In order that the disclosure may be readily understood, aspects of this disclosure are illustrated by way of examples in the accompanying drawings.

The same or similar reference numbers are used in the drawings and the following detailed description to refer to the same or similar parts.

DETAILED DESCRIPTION

The invention will now be described with reference to the figures, in which like reference numerals refer to like parts throughout. In accordance with conventional practice, as used herein, and unless otherwise indicated herein, the term "proximal portion" refers to the specified portion of a device or its component which is generally closer to the medical personnel handling or manipulating the device as it is intended to be used, and the term "distal portion" shall may refer to the specified portion of a device or its component which is opposite the proximal portion.

The present invention is generally directed to a clip applier having replaceable applier tips. The applier tips may be securing members configured to be loaded onto jaw members of the clip applier prior to loading a surgical clip onto the clip applier. The applier tips may be releasably secured to the jaw members by receiving the jaw members in a sleeve portion of the applier tips and interlocking an arm on the sleeve portion with a groove on the respective jaw member. After applying one or more of the surgical clips, the applier tips may be removed from the clip applier and disposed of. One or more applier tips may be housed in a common cartridge (but separate compartments) as one or more surgical clips for convenience in loading the clip applier device. The applier tips may be separate and unconnected, when not secured to the clip applier. Regularly replacing the applier tips may ensure sterility and reduce wear of interlocking parts of the applier tips.

The applier tips may provide at least three-points of contact with the surgical clip, which may ensure alignment of the surgical clip and prevent lateral movement (e.g., fishtailing) of the surgical clip during application. The applier tips may have one or more recesses on a distal portion configured to engage a boss member on a distal portion of the surgical clip. The distal portion of the applier tips may include first and second distal extensions from the sleeve portion. Each of the distal extensions may have a recess configured to receive opposing boss members of the surgical clip. The applier tips may also have a protrusion extending from an inner portion of the sleeve portion off-center of the longitudinal axis, such that a proximal end (e.g., a hinge member) of the surgical clip may be received in a space between protrusions of opposing applier tips. The opposing protrusions may prevent the proximal end of the surgical clip from fish-tailing during loading and/or application with the clip applier. The protrusion may be in the shape of a wall or fin and have opposing substantially flat side surfaces. The applier tips may be formed of an inexpensive, disposable plastic, and the clip applier may be formed of a more durable, re-usable metal.

Figure 1:
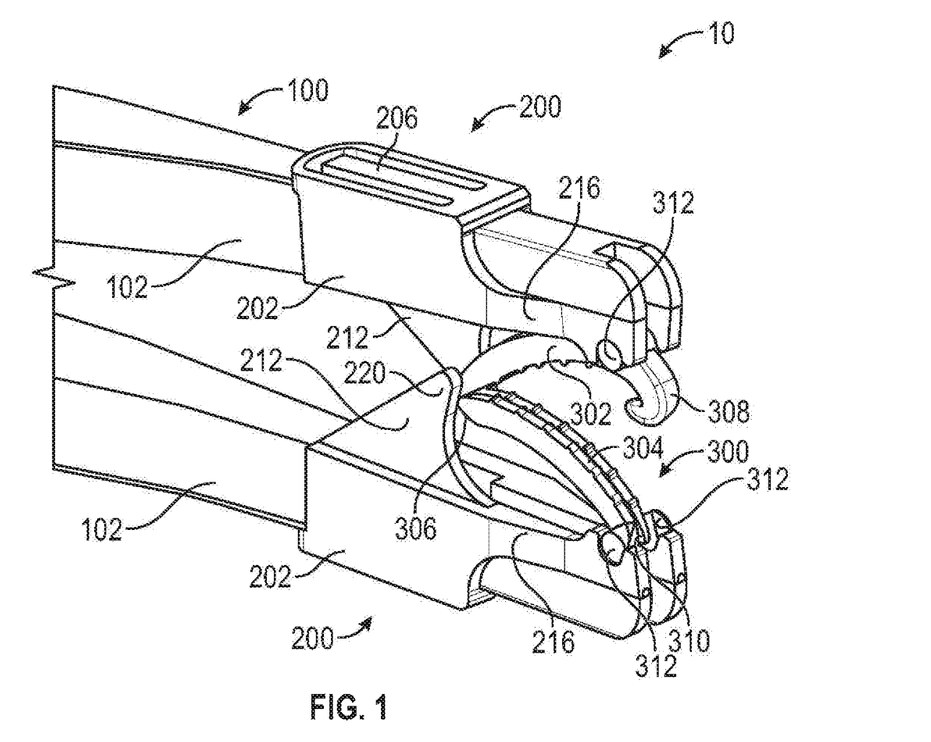
FIG. 1 illustrates a first embodiment of an exemplary clip applier device having exemplary applier tips and loaded with an exemplary surgical clip of the present disclosure.

FIG. 1 illustrates a clip applier device 10 of the present disclosure. As illustrated, the clip applier device 10 may include a clip applier 100 and one or more applier tips 200 configured to receive a surgical clip 300 from a cartridge 400. The clip applier device 10 may secure the surgical clip 300 during loading of the surgical clip 300, delivery of the surgical clip 300 to tissue, and application of the surgical clip 300 to tissue.

The surgical clip 300 may comprise a first leg member 302 and a second leg member 304 pivotably joined with a hinge member 306. The first leg member 302 may have a generally concave inner surface, a generally convex outer surface, and a hook member 308 on a distal portion. The second leg member 304 may have a generally convex inner surface, a generally concave outer surface, and a tip member 310 on a distal portion. The surgical clip 300 may be configured to be applied to tissue (e.g., ligate a blood vessel) by applying compression to the first and second leg members 302, 304. The hook member 308 may engage and deflect around the tip member 310, while one or both of the first and second leg members 302, 304 straighten and lengthen. The tip member 310 may then be received in the hook member 308 to secure the surgical clip 300 in a latched configuration. Each of the first and second leg members 302, 304, may have one or more boss members 312 on a distal portion configured to engage the applier tips 200. An exemplary embodiment of the surgical clip 300 is further described in U.S. Pat. No. 4,834,096, the disclosure of which is expressly incorporated herein in its entirety. However, it is contemplated that the clip applier device 10 may be configured to apply any number of configurations of the surgical clip 300.

The clip applier 100 may include first and second jaw members 102 pivotably coupled at a hinge member 104. The clip applier 100 may be actuatable between open and closed configurations by any number of handle mechanisms (not shown). The clip applier 100 may also include a biasing mechanism (not shown) configured to bias the jaw members 102 into the open configuration. For example, the biased, open configuration may align the first and second jaw members 102 with apertures of one or more compartments of the cartridge 400 to facilitate loading of the applier tips 200 and/or the surgical clip 300. The jaw members 102 may be configured to not directly contact the surgical clip 300.

Figure 3:
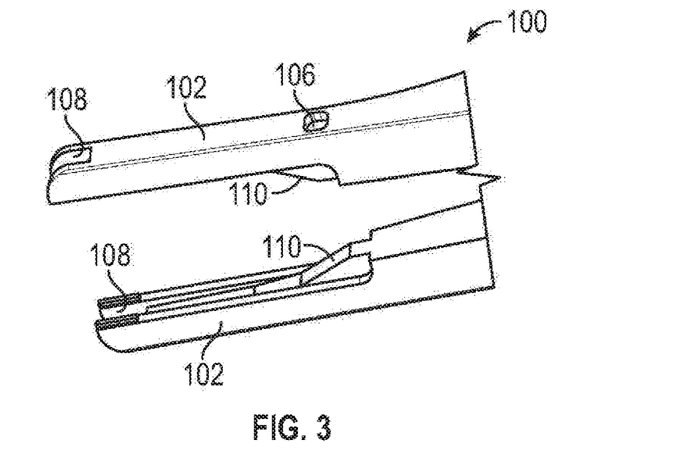
FIG. 3 illustrates a perspective view of an exemplary clip applier of the first embodiment of FIG. 1.

Each of the first and second jaw members 102 may be configured to releasably receive an applier tip 200 thereon. The first and second jaw members 102 may include a recess 106 positioned on an outer surface (as further illustrated in FIG. 3) and configured to releasably secure the applier tips 200 to the clip applier 100. The first and second jaw members 102 may further include an open distal portion 108 and a projecting member 110 on an inner portion extending along a central axis.

The applier tips 200 (as further illustrated in FIGS. 2A-B) may include a sleeve portion 202 configured to receive one of the jaw members 102. The sleeve portion 202 may have an outer channel 204 housing a flexible arm 206 with a projection 208 on its free end. The flexible arm 206 may be pivotably secured to the sleeve portion 202 and configured to deflect outward as one of the jaw members 102 is inserted into the sleeve portion 202. As the jaw member 102 is advanced through the sleeve portion 202, the flexible arm 206 may pivot back toward a relaxed state, such that the projection 208 may be received in the recess 106 to releasably interlock the applier tip 200 to the jaw member 102. The engagement between the applier tips 200 and the jaw members 102 may be sufficient to secure the surgical clip 300 onto the clip applier 100. The applier tips 200 may also be removed and/or disposed of after application of one or more surgical clips 300.

Figure 2A:
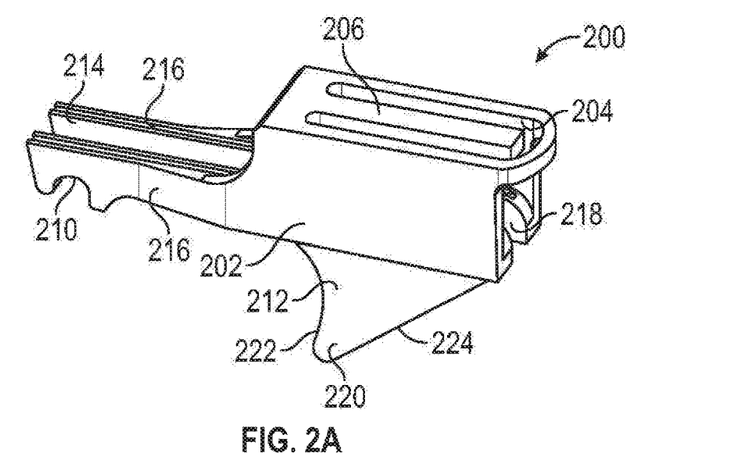
FIGS. 2A-B illustrate perspective views of the exemplary applier tip of the first embodiment of FIG. 1.
Figure 2B:
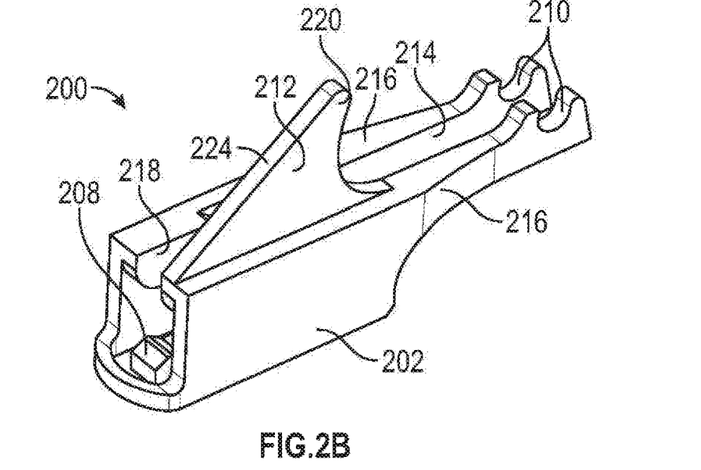

As further illustrated in FIGS. 2A-B, the applier tips 200 may include at least one recess 210 at a distal portion and a protrusion 212 at a proximal portion. The recess 210 may extend transversely through the applier tips 200 and be configured to receive a boss member 312 on leg members 302 of the surgical clip 300 in an interference or snap-fit. The applier tips 200 may further include an inner channel 214 extending through the inner portion of the applier tips 200. The inner channel 214 may separate the distal portion into first and second extensions 216 extending from the sleeve portion 202, such that the sleeve portion 202 may not extend the entire length of the applier tips 200. Each of the extensions 216 may have a recess 210 configured to receive opposing boss members 312. The inner channel 214 may also include a narrow proximal portion 218 configured to receive the projecting member 110 on the inner portion of the jaw members 102, increasing lateral stability of the applier tips 200.

The protrusion 212 may be configured to align the surgical clip 300 by reducing lateral movement of a proximal portion (e.g., the hinge member 306). The protrusions 212 may extend inwardly from the sleeve portion 202 and off-center of a longitudinal axis of the applier tip 200. Protrusions 212 of opposing applier tips 200 may therefore form a space that receives the proximal portion of the surgical clip 300 and reduces relative movement in either lateral direction. The protrusions 212 may be in the form of a wall or a fin having substantially flat side surfaces that do not hinder closure of the surgical clip 300. The protrusions 212 may also allow the curved leg members to lengthen as the surgical clip 300 closes, and the hook member 308 deflects around the tip member 310. In that sense, the applier tips 200 may not have any portion positioned proximal of the surgical clip 300 that impedes proximal lengthening of the leg members 302, 304. The protrusions 212 may have a tip portion 220 adjacent and substantially parallel with the proximal portion (e.g. the hinge member 306) of the surgical clip 300 when the jaw members 102 are in an open configuration. However, in some embodiments, the tip portions 220 of opposing protrusions 212 may not overlap each other in the open configuration. The tip portion 220 may be formed at the junction of a concave distal portion 222 and a substantially flat angled proximal portion 224. The protrusions 212 may slide vertically along opposing sides of the surgical clip 300, as the jaw members 102 pivot and close the surgical clip 300.

Although FIGS. 1-2B illustrate a protrusion 212 on each of the first and second applier tips 200, it is also contemplated that both protrusions 212 may be disposed on one of the applier tips 200, such that the protrusion 212 on the opposing jaw member 102 and/or applier tip 600 may be omitted. It is further contemplated that one of the applier tips 200 may be omitted, such that the clip applier 100 may be configured to only receive a single applier tip 200 and the one or more recess 210 and/or protrusion 212 may be integrated into the opposing jaw member 102. Therefore, in some unillustrated embodiments, the clip applier device 10 may include a single applier tip 200 having one or more recesses 210 and first and second protrusions 212 disposed inwardly, and the opposing jaw member 102 having one or more recesses 210 formed integrally and not having a protrusion 212.

Figure 4A:
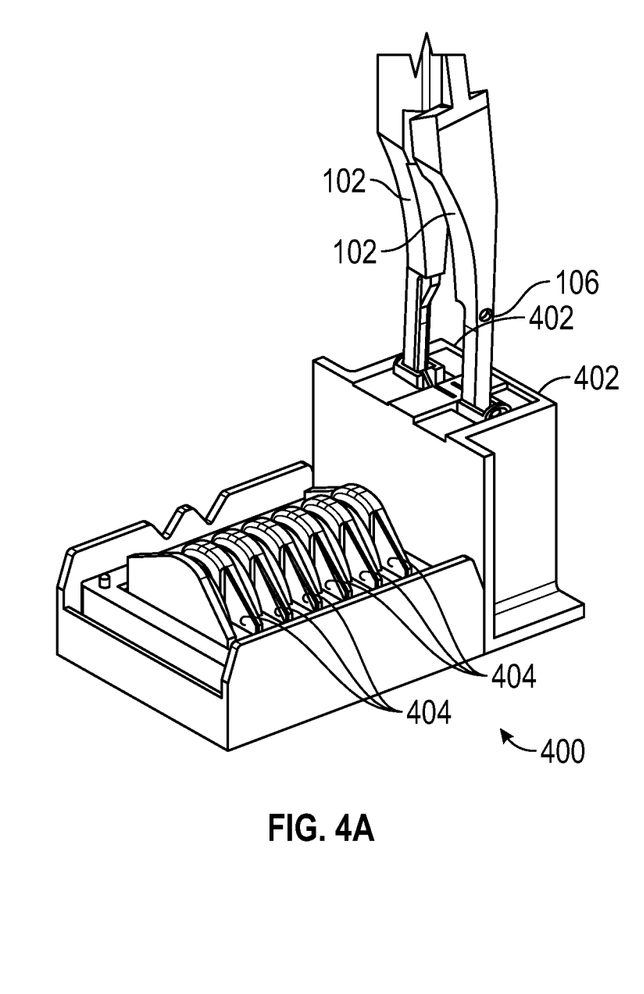
FIGS. 4A-B illustrate an exemplary method of assembling and loading the first embodiment of FIGS. 1-3.
Figure 4B:
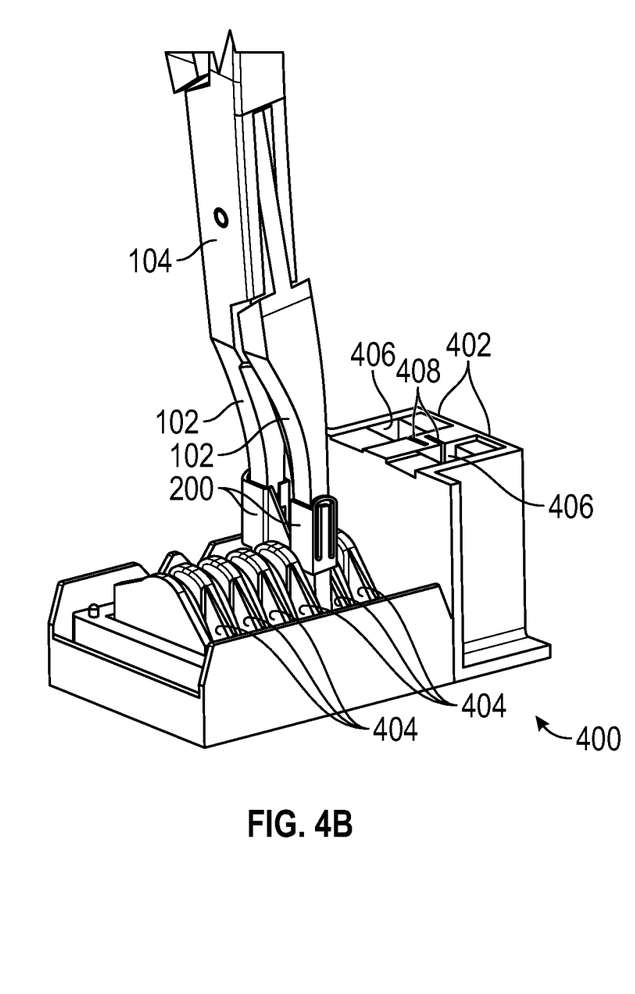

As illustrated in FIGS. 4A-B, the clip applier device 10 may be assembled by receiving the applier tips 200 and/or the surgical clip 300 from the cartridge 400. The cartridge 400 may include one or more tip compartments 402 containing an applier tip 200 and/or one or more clip compartments 404 containing at least one surgical clip 300. For example, the cartridge 400 may include first and second tip compartments 402 structurally rotated 180 degrees relative to each other to receive Opposing jaw members 102. The tip compartments 402 may include an aperture configured to receive the jaw members 102 when in an open configuration. The tip compartments 402 may include a first portion 406 aligned with the aperture and configured to house the sleeve portion 202 of the applier tip 200. The tip compartments 402 may also include a second portion 408 configured to house the protrusion 212 of the applier tip 200, where the second portion 408 is narrower than the first portion 406. As illustrated in FIGS. 4A-B, the second portions 408 of the tip compartments 402 may overlap to ensure proper alignment with the jaw members 102. The cartridge 400 may further include a plurality of clip compartments 404 aligned along a longitudinal axis of the cartridge 400. The number of clip compartments 404 may be based on the the applicable surgical procedure. In some embodiments, each of the tip compartments 402 may house a single applier tip 200, and each of the clip compartments 404 may house a single surgical clip 300.

As further illustrated in FIGS. 4A-B, the clip applier device 10 may be assembled according to a method including inserting each of the jaw members 102 into the first portion 406 of the tip compartment 402 to secure an applier tip 200 to each of the jaw members 102. The applier tips 200 may be substantially identical, but rotated 180 degrees to be symmetrically arranged on the first and second jaw members 102, as illustrated in FIG. 1. The applier tips 200 may be secured to the jaw members 102 by receiving the jaw member 102 into the sleeve portion 202 of the applier tip 200 and receiving the projection 208 into the recess 106 of the jaw member 102. The method may further include inserting the jaw members 102 into the clip compartment 404 to secure the surgical clip 300 to the applier tip 200. For example, the applier tips 200 may receive a boss member 312 of the surgical clip 300 in the recesses 210 and the hinge member 306 of the surgical clip 300 between opposing protrusions 212. The clip applier 100 may be configured to compress and/or latch the loaded surgical clip 300 onto tissue. The clip applier 100 may then be loaded with a second surgical clip 300 using the same applier tips 200 for the second surgical clip 300 to be applied during the same procedure. The applier tips 200 may then be removed from the clip applier 100 and/or disposed of following the procedure.

Figure 5:
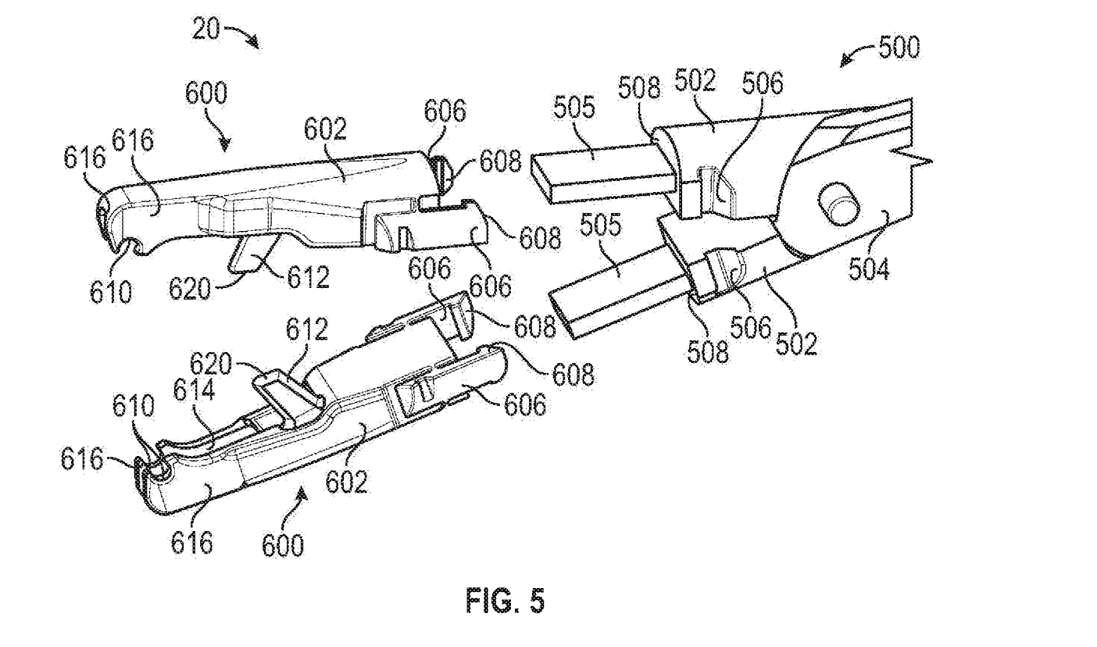
FIG. 5 illustrates a perspective view of a second embodiment of an exemplary clip applier device having exemplary applier tips of the present disclosure.
Figure 6:
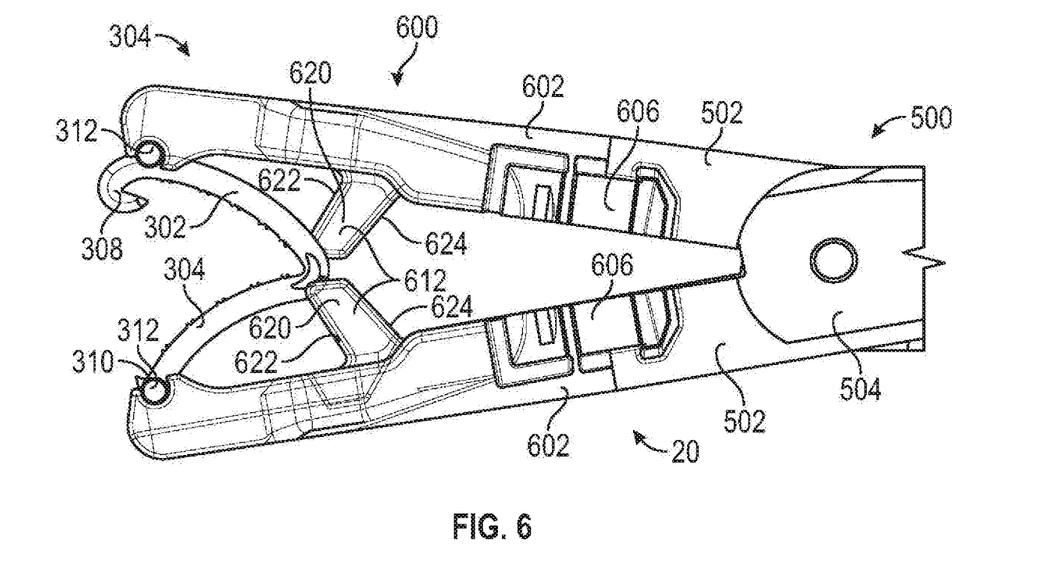
FIG. 6 illustrates a side view of the second embodiment of FIG. 5 loaded with an exemplary surgical clip.

FIGS. 5-6 illustrate a clip applier device 20 of the present disclosure. As illustrated, the clip applier device 20 may include a clip applier 500 releasably coupled to at least one applier tip 600.

The clip applier 500 may include first and second jaw members 502 pivotably coupled at a hinge member 504. The clip applier 500 may be actuatable between open and closed configurations by any number of handle mechanisms (not shown). The clip applier 500 may also include a biasing mechanism (not shown) configured to bias the jaw members 502 into the open configuration. For example, the biased open configuration may align the jaw members 502 with apertures of one or more of compartments of a cartridge to facilitate the loading of the applier tips 600 and/or the surgical clip 300. The jaw members 502 may be configured to not directly contact the surgical clip 300. Each of the jaw members 502 may be configured to receive an applier tip 600 thereon.

As illustrated in FIG. 5, the jaw members 502 may have a shank portion 505 with a reduced height and width relative to the portion of the jaw members 502 immediately proximal of the shank portion 505. The jaw members 502 may have a substantially flat distal facing surface 508 formed at the junction between the shank portion 505 and the immediately proximal portion. The flat distal facing surface 508 may provide a backstop to the applier tips 600 and ensure a continuous alignment between the applier tips 600 and the jaw members 502, as illustrated in FIG. 6. The jaw members 502 may also include one or more recesses 506 proximal of the shank portion 505. The recesses 506 may be positioned on each side surface of the jaw members 502 and may be configured to releasably secure the applier tips 600 to the clip applier 100.

The applier tips 600 may include a sleeve portion 602 configured to receive the shank portions 505 of the jaw members 502. The sleeve portion 602 may have a flexible arm 606 extending proximally from the sleeve portion 602. The flexible arm 606 may have a projection 608 on its free end. The flexible arm 606 may be pivotably secured to the sleeve portion 602 and configured to deflect outward as one of the shank portion 505 is inserted into the sleeve portion 602. As the shank portion 505 is advanced through the sleeve portion 602, the flexible arm 606 may pivot back toward a relaxed state, such that the projection 608 may be received in the recess 506 to releasably interlock the applier tip 600 to the jaw member 502. The engagement between the applier tips 600 and the jaw members 502 may be sufficient to secure the surgical clip 300 onto the clip applier 500. The applier tips 600 may also be removed and/or disposed of after application of one or more surgical clips 300. As further illustrated in FIGS. 5 and 7B, the flexible arm 606 may be attached to the sleeve portion 602 at a central pivot, between proximal and distal ends of the flexible arm 606. The central pivot of the flexible arm 606 may allow removal of the applier tips 600 by applying pressure at a distal portion of the flexible arm 606, as illustrated in FIG. 7B. The flexible arm 606 may further include a notch at the distal portion to facilitate removal, for example, by receiving a ridge 704 of a removal device 700 (as illustrated in FIG. 7B).

As further illustrated in FIGS. 5-6, the applier tips 600 may include at least one recess 610 at a distal portion and a protrusion 612 at a portion proximal of the at least one recess 610. The recess 610 may be configured to receive a boss member 312 on leg members 302 of the surgical clip 300 in an interference or snap-fit. The applier tips 600 may further include an inner channel 614 extending through the inner portion of the applier tips 600. The inner channel 614 may separate the distal portion into first and second extensions 616 extending from the sleeve portion 602, such that the sleeve portion 602 may not extend the entire length of the applier tips 600. Each of the extensions 616 may have a recess 610 configured to receive opposing boss members 312.

The protrusion 612 may be configured to align the surgical clip 300 by reducing lateral movement of a proximal portion (e.g., the hinge member 306). The protrusions 612 may extend inwardly from the sleeve portion 602 and off-center of a longitudinal axis of the applier tip 600. Protrusions 612 of opposing applier tips 600 may form a space that receives the proximal portion of the surgical clip 300 and reduces relative lateral movement in either lateral direction. The protrusions 612 may be in the form of a wall or a fin having substantially flat side surfaces that do not hinder closure of the surgical clip 300. The protrusions 612 may also allow the curved leg members to length as the surgical clip 300 closes, and the hook member 308 deflects around the tip member, in that sense, the applier tips 600 may not have any portion positioned proximally of the surgical clip 300 that impedes proximal lengthening of the leg members 302, 304. The protrusions 612 may have a tip portion 620 adjacent and substantially parallel with the proximal portion (e.g. the hinge member 306) of the surgical clip 300 when the jaw members 502 are in an open configuration. However, in some embodiments, the tip portions 620 of opposing protrusions 612 may not overlap each other in the open configuration. The tip portion 620 may be formed by a substantially flat angled distal portion 622 and a substantially flat angled proximal portion 624. Each of the flat angled distal and proximal portions 622, 624 may extend distally at an acute angle. The protrusions 612 may slide vertically along opposing sides of the surgical clip 300, as the jaw members 502 pivot and close the surgical clip 300.

Although the FIGS. 5-6 illustrate a protrusion 612 on each of the first and second applier tips 600, it is also contemplated that both protrusions 612 may be disposed on one of the applier tips 600, such that the protrusion 612 on the opposing jaw member 502 and/or applier tip 600 may be omitted. It is further contemplated that one of the applier tips 600 may be omitted, such that the clip applier 500 may be configured to only receive a single applier tip 600 and the opposing jaw member 102 may have one or more recess 610 and/or protrusion 612 integrally formed. Therefore, in some unillustrated embodiments, the clip applier device 20 may include a single applier tip 600 having one or more recesses 610 and first and second protrusions 612 disposed inwardly, and the opposing jaw member 502 having one or more recesses 610 formed integrally and not having a protrusion 612.

To assemble the clip applier device 20, the applier tips 600 may be initially stored in a tip compartment of a cartridge (e.g., as illustrated in FIGS. 4A-B). The sleeve portion 602 of the applier tip 600 may then receive the shank portion 505 of the jaw members 502, and the recess 506 of the jaw members 502 may receive the projection 608 of the arm 606 of the applier tip 600. The shank portion 505 of the clip applier 500 may have a reduced width and thickness to allow for the clip applier device 20 to have a continuous inner and/or outer surface transition from the clip applier 500 to the applier tips 600, as illustrated in FIG. 6. As discussed above, the applier tips 600 may secure the surgical clip 300 with engagements between the recesses 610 and the boss members 312 and receiving the hinge member 306 between the protrusions 612.

Figure 7A:
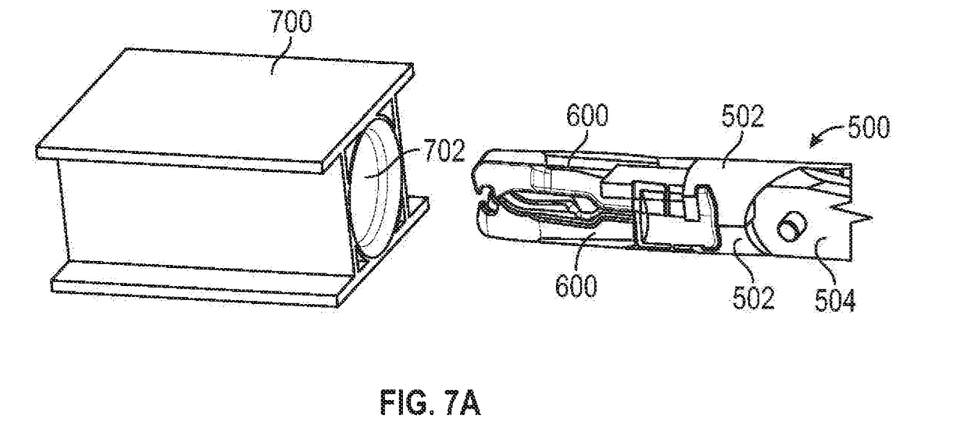
FIGS. 7A-B illustrate an exemplary removal device removing the exemplary applier tips from the second exemplary embodiment of FIGS. 5-6.
Figure 7B:
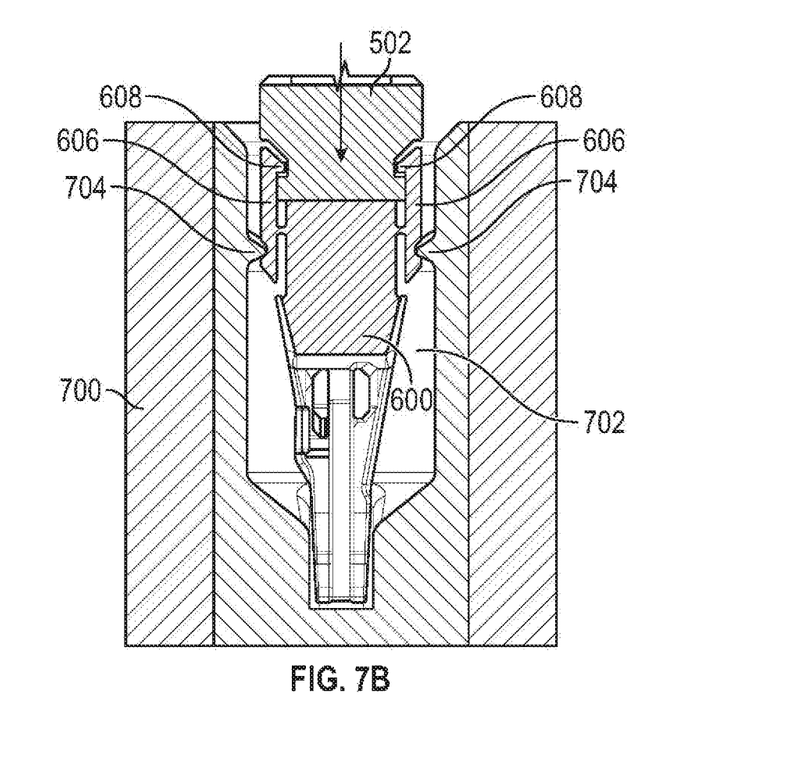

FIGS. 7A-B illustrate a removal device 700 for removing the applier tips 600 from the clip applier 500. The removal device 700 may include a longitudinal bore 702 configured to receive the clip applier device 20. The longitudinal bore 702 may have an interior wall with ridges 704 configured to engage a distal portion of the arms 606 to pivot the arms 606 and lift the projections 608 out of the recess 512 of the clip applier 500. The clip applier 500 may then be retracted out of the removal device 700, and the applier tips 600 may be retained in the longitudinal bore 702.

The various embodiments of the applier tips and clip applier devices may therefore provide at least three-points of contact with the surgical clip. The applier tips may engage the distal portion of the surgical clip with the engagement of the recesses to the boss members, and the applier tips may laterally align the surgical clip by receiving the proximal portion of the surgical clip between the opposing protrusions. The opposing protrusions may reduce lateral movement of the proximal portion and prevent the surgical clip from fish-tailing.

The surgical clip 300 of the present disclosure may be made of any suitable size and may be applied to any number of tissues, such as blood vessels, lymph nodes, nerves, fallopian tubes, or cardiac tissue. The surgical clip 300 may be constructed from any suitable biocompatible material, such as certain metals and polymers. However, the present invention is particularly suitable for practice with polymeric clips. Thus, the surgical clip 300 preferably has a one-piece integral polymeric body formed from a suitable strong biocompatible engineering plastic such as the type commonly used for surgical implants. Exemplary materials include homopolymer or co-polymer polyacetal, polyethylene terephthalate (PET), polybutylene terephthalate (PBT), polyoxymethylene, or other thermoplastic materials having similar properties that can be injection-molded, extruded or otherwise processed into like articles.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A clip applier assembly configured to be loaded with a surgical clip, the clip applier assembly comprising:
    a clip applier having first and second jaw members;
    a first applier tip releasably secured to the first jaw member, the first applier tip having a first protrusion with a first tip portion; and
    a second applier tip releasably secured to the second jaw member, the second applier tip having a second protrusion with a second tip portion,
    wherein the first and second applier tips are configured to secure the surgical clip to the first and second jaw members with a portion of the surgical clip between the first tip portion and the second tip portion.

2. A method of securing a surgical clip to the clip applier assembly of claim 1, the method comprising:
    engaging the first applier tip with the first jaw member;
    engaging the second applier tip with the second jaw member;
    receiving the surgical clip between the first and second jaw members; and
    securing the surgical clip with the first and second applier tips to the clip applier.

3. The method of claim 2, further comprising aligning the surgical clip by receiving a proximal portion of the surgical clip between the first protrusion of the first applier tip and the second protrusion of the second applier tip.

4. The method of claim 2,
    wherein securing the surgical clip with the first applier tip includes receiving a first boss member on a first leg member of the surgical clip in a recess of the first applier tip, and
    wherein securing the surgical clip with the second applier tip includes receiving a second boss member on a second leg member of the surgical clip in a recess of the second applier tip.

5. The method of claim 2, further comprising:
    inserting the first and second jaw members into at least one first compartment of a cartridge to engage the first applier tip and the second applier tip; and
    inserting the first and second jaw members into a second compartment of the cartridge to receive the surgical clip between the first and second jaw members.

6. The method of claim 2, further comprising:
    inserting the first jaw member into a first sleeve portion of the first applier tip; and
    inserting the second jaw member into a second sleeve portion of the second applier tip.

7. The method of claim 2,
    wherein engaging the first applier tip includes releasably securing an engaging member on the first applier tip to an engaging member on the first jaw member, and
    wherein engaging the second applier tip includes releasably securing an engaging member on the second applier tip to an engaging member on the second jaw member.

8. The method of claim 2,
    wherein engaging the first applier tip includes deflecting a first flexible arm of the first applier tip and receiving a first projection on the first flexible arm in a recess of the first jaw member, and
    wherein engaging the second applier tip includes deflecting a second flexible arm of the second applier tip and receiving a second projection on the second flexible arm in a recess of the second jaw member.

9. The method of claim 2, further comprising:
approximating the first and second jaw members to compress the surgical clip;
removing the first applier tip from the first jaw member; and
removing the second applier tip from the second jaw member.

10. The clip applier assembly of claim 1, wherein the first protrusion extends from an inner surface of the first applier tip, the second protrusion extends from an inner surface of the second applier tip, and the first and second protrusions are configured to receive a proximal portion of the surgical clip therebetween to reduce lateral movement of the surgical clip.

11. The clip applier assembly of claim 1, wherein the first and second protrusions extend offset from a longitudinal axis of the first and second applier tips.

12. The clip applier assembly of claim 1,
wherein the first applier tip comprises a first recess at a distal portion configured to receive a boss member on a first leg member of the surgical clip, and
wherein the second applier tip comprises a second recess at a distal portion configured to receive a boss member on a second leg member of the surgical clip.

13. The clip applier assembly of claim 1,
wherein the first applier tip comprises a first sleeve portion receiving the first jaw member, and
wherein the second applier tip comprises a second sleeve portion receiving the second jaw member.

14. The clip applier assembly of claim 13,
wherein the first sleeve portion comprises an engaging member releasably secured to an engaging member of the first jaw member, and
wherein the second sleeve portion comprises an engaging member releasably secured to an engaging member of the second jaw member.

15. The clip applier assembly of claim 14,
wherein the engaging member of the first sleeve portion comprises a first flexible arm having a first projection, and the engaging member of the first jaw member comprises a first recess receiving the first projection, and
wherein the engaging member of the second sleeve portion comprises a second flexible arm having a second projection, and the engaging member of the second jaw member comprises a second recess receiving the second projection.

16. The clip applier assembly of claim 13,
wherein the first sleeve portion is on a proximal portion of the first applier tip and extends less than an entire length of the first applier tip, and
wherein the second sleeve portion is on a proximal portion of the second applier tip and extends less than an entire length of the second applier tip.

17. A clip applier assembly configured to be loaded with a surgical clip, the clip applier assembly comprising:
a clip applier having first and second jaw members;
a first applier tip releasably secured to the first jaw member, wherein the first applier tip comprises a first sleeve portion receiving the first jaw member, the first sleeve portion comprises a first flexible arm having a first projection, and the first jaw member comprises a first recess receiving the first projection; and
a second applier tip releasably secured to the second jaw member wherein the second applier tip comprises a second sleeve portion receiving the second jaw member, the second sleeve portion comprises a second flexible arm having a second projection, and the second jaw member comprises a second recess receiving the second projection,
wherein the first and second applier tips are configured to secure the surgical clip between the first and second jaw members.

18. The clip applier assembly of claim 17, wherein the first applier tip comprises a first protrusion extending from an inner surface, and the second applier tip comprises a second protrusion extending from an inner surface, the first and second protrusions being configured to receive a proximal portion of the surgical clip therebetween to reduce lateral movement of the surgical clip.

19. The clip applier assembly of claim 17, wherein the first and second protrusions extend offset from a longitudinal axis of the first and second applier tips.

20. The clip applier assembly of claim 17,
wherein the first applier tip comprises a first recess at a distal portion configured to receive a boss member on a first leg member of the surgical clip, and
wherein the second applier tip comprises a second recess at a distal portion configured to receive a boss member on a second leg member of the surgical clip.

* * * * *